US00PP12178P2

(12) United States Plant Patent
Zerr

(10) Patent No.: US PP12,178 P2
(45) Date of Patent: Oct. 30, 2001

(54) POINSETTIA PLANT NAMED 'FISGALA'

(75) Inventor: Katharina Zerr, Simmern (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/210,122

(22) Filed: Dec. 11, 1998

(51) Int. Cl.[7] ..... A01H 5/00
(52) U.S. Cl. ..... Plt./307
(58) Field of Search ..... Plt./307

(56) References Cited

U.S. PATENT DOCUMENTS

P.P. 9,336 * 10/1995 Beckmann ..... Plt./306
4,724,276 * 2/1988 Ecke, Jr. ..... 47/58

OTHER PUBLICATIONS

UPOV–ROM GTITM Computer Database 1000/02, GTI JOUVE Retrieval Software, citations for 'Fisgala', May 1999.*

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

'Fisgala' is characterized by dark-red flower color bracts that are medium-sized and ovate with occasionally with weak lobes; dark-green foliage which is moderately lobed; relatively early flowering response; and moderately vigorous growth with average plant height and upright plant habit during vegetative stage.

1 Drawing Sheet

BACKGROUND OF THE INVENTION

The present invention relates to a new and distinct cultivar of Poinsettia plant known by the cultivar name 'Fisgala' and botanically known as *Euphorbia pulcherrima.*

'Fisgala' is a product of a planned breeding program which had the objective of creating new poinsettia cultivars with red bract color, dark-green foliage, good branching characteristics and early flowering response. 'Fisgala' was originated from hybridization made in a controlled breeding program in Hillscheid, Germany, in 1994.

The female parent was a proprietary hybrid seedling No. S90-1202-1 characterized by bright-red bract color, medium-green foliage and very compact habit. The male parent was a hybrid seedling No. S90-502-1, with red-colored bracts, dark-green foliage and early flowering. 'Fisgala' was discovered and selected as one flowering plant (No. 4747) within the progeny of the stated parentage by Katharina Zerr in autumn of 1995 in a controlled environment in Hillscheid, Germany.

The seeds from the cross-germination in February of 1995 and the seedlings were identified by numbers. In summer of 1995 in Hillscheid, Germany, a cutting was taken from each seedling and grown as a flowering, single-stem plant for examination in autumn and winter. The cuttings used were grown shoot tips (short stem with 3–4 mature leaves) from the upper area of the plant, taken from branches emerging from the main stem higher than the place of the grafting. After plant No. 4747 had been chosen, more cuttings were taken from the original seedling and grafted on rootstocks of variety 'Beckmanns Altrosa' (U.S. Plant Pat. No. 9,336) in order to transmit the branching-causing agent into the clone. The branch causing agent is a Phytoplasma which is transmitted by grafting. With branched plants grown from cuttings of the grafted plants, another trial cultivation (horticultural examination) took place in autumn and winter 1996/97.

Horticultural examination initiated in autumn of 1996 and continuing thereafter has demonstrated that the combination of characteristics as herein disclosed for 'Fisgala' are firmly fixed and are retained through successive generations of asexual reproduction.

BRIEF DESCRIPTION OF THE INVENTION

The following traits have been repeatedly observed and are determined to be basic characteristics of 'Fisgala' which in combination distinguish this Poinsettia as a new and distinct cultivar:

1. Dark-red bract color;
2. Medium-sized ovate bracts, occasionally with weak lobes;
3. Dark-green foliage, moderately lobed;
4. Relatively early flowering response; and
5. Moderately vigorous growth, average height, upright plant habit during vegetative stage.

'Fisgala' has not been observed under all possible environmental conditions. The phenotype may vary significantly with variations in environment such as temperature, light intensity, and daylength without a change in genotype. The following observations, measurements and comparisons describe plants grown in Hillscheid, Germany, and Langley, British Columbia, Canada, under greenhouse conditions which approximate those generally used in commercial practice.

Of the many commercial varieties known to the inventor, the most similar in comparison to 'Fisgala' are the patented cultivars 'Freedom Red' (U.S. Plant Pat. No. 7,825) and 'Fiscor' (U.S. Plant Pat. No. 9,364). In comparison to 'Freedom Red', 'Fisgala' has a darker and more stable red bract color, which does not tend to fade at high temperatures. Bracts and leaves of 'Fisgala' are smaller in size than those of 'Freedom Red' and flowering response is a few days later than 'Freedom Red'. In comparison to 'Fiscor', 'Fisgala' has slightly darker red-colored bracts, a taller and less wide plant habit, and earlier flowering response. The cultivars 'Fisnova', 'Fismille' and 'Fisgala' are compared below.

| | FISNOVA | FISMILLE | FISGALA |
|---|---|---|---|
| Bract color | medium to dark red | Brilliant, medium red | Dark red, often more |
| Upper Surface RHS | 46 B | 45 A | bluish than: 46 B |
| Lower Surface RHS | 46 B–C | 46 B | 46 B |
| Stem color | Light to medium green, | Medium green, | Medium green, |
| Infusion of anthocyanin | 137 C weak | 137 B weak | 137 B strong |
| Foliage, lobes | weak | almost no lobes | weak to medium |
| Growth/Plant habit | Medium vigor, rel. compact as a young plant, develops later a more round plant habit when given enough space so that all the branches may develop fairly evenly * | vigorous, medium to tall, upright plant habit | moderately vigorous growth, medium height, V-shaped plant habit with uniformly developed branches |
| No. of branches | 8.5 | 6.9 | 7.5 |
| Begin of flowering | 8.5 weeks | 7.5 weeks | 8–8.5 weeks |

BRIEF DESCRIPTION OF THE DRAWING

The accompanying color photographic sheet shows typical inflorescence and foliage of a mature potted plant of 'Fisgala', with colors being as true as possible with illustrations of this type.

DETAILED BOTANICAL DESCRIPTION

The plants described herein were grown in a greenhouse in Langley, British Columbia, Canada, in the autumn of 1997. Rooted cuttings were planted into 15-cm pots on August 1, and were pinched on August 18, leaving 8 nodes. The minimum temperature was 23° C. until October 10, 20° C. to mid-November, and lower thereafter. The plants initiated flowers under natural short-day conditions in autumn.

In the following description, color references are made to The Royal Horticultural Society Colour Chart (R.H.S.). The color values were determined indoors in a north light.

Classification:

*Botanical.*—*Euphorbia pulcherrima.*

*Commercial.*—Poinsettia, cv. 'Fisgala'.

Parentage:

*Female parent.*—Hybrid seedling No. S 90-1202-1.

*Male parent.*—Hybrid seedling No. S 90-502-1.

Plant:

*Form.*—Shrub, self-branching.

*Growth habit.*—Moderately vigorous growth, average height, with branches at a narrow acute angle (upright directed) during vegetative stage. Branches develop in a relatively uniform way, thus producing/forming bracts (not single bracts, but whole inflorescences) of almost equal size. Height, including pot, is 45.5 cm. The average number of branches is 7.5.

*Rooting.*—Medium, about 20–24 days.

*Stem color.*—Medium-green, RHS 137 B, with a relatively strong infusion of anthocyanin, RHS 181 A or RHS 184 B.

*Blooming habit.*—Flowering response time under natural short-day conditions in autumn: botanically, cyathia open, in late November; commercially, bracts colored and marketable, around November 24.

*Flowering response time.*—8 to 8.5 weeks.

*Keeping Quality after Sale ('Shelf Life').*—Good, above average of the group of dark-foliaged varieties. Depending on cultivation conditions, quality can last 28–35 days in conditions as described in Langley, Canada.

Foliage:

*Shape.*—Narrow ovate, moderately lobed, and with acuminated tip.

*Margin.*—Entire.

*Texture.*—Upper surface: Smooth and flat, only weakly veined, veins are often hardly visible and are light-green, RHS 146 D or red, near RHS 46 B, especially with younger leaves and at the base of mature leaves, the basal part of the midrib has a reddish color similar to the petiole. Lower surface: Flat and smooth, except for the slightly protruding midrib and finer side veins, arranged in a 'herringbone' pattern; the vein color is light-green, RHS 139 D to dull pink, RHS 182 B or lighter.

*Size.*—Leaf blade length is 13.3 cm; leaf blade width is 9.0 cm; petiole length is 6.8 cm.

*Color.*—Generally a uniform dark-green. Mature foliage: upper surface is RHS 139 A; under surface is RHS 137 B. New foliage: upper side is about RHS 143 A; under side is about RHS 143 C to D.

*Petiole color.*—Red to dark-red, relatively intense, near RHS 53 A.

*Aspect.*—Petioles and leaves are directed slightly upward during vegetative growth stage.

*Disease resistance.*—Typical, no special observations made.

Flowering description:

*Inflorescence.*—Medium-sized, horizontally directed with the bracts nearly flat. The diameter of inflorescence is 27.0 cm.

*Size of bract.*—The length is 13.5 cm and width is 9.0 cm; petiole is 2.5 cm.

*Number of leaves per plant.*—Undetermined.

*Number of inflorescence per plant.*—6.5–7.

*Number of bracts per inflorescence.*—10–13 true bracts, length over 2 cm.

*Bracts, shape.*—Ovate-shaped with rounded base, acuminated tip, and occasionally with weak lobes.

*Texture.*—Relatively smooth or slightly rugose, nearly flat; the veins are arranged in a herringbone pattern and are hardly visible; the vein color corresponds to the bract color of the upper surface, while the veins on the lower surface are usually lighter, brownish-pink, RHS 47 A or lighter.

*Color.*—Generally an intense dark-red with a slight bluish hue, uniform, and without tendency to fading near the margin, and intense red (no fading) in summer culture. Upper surface: Near RHS 46 B. Lower surface: More bluish hue than RHS 46 B.

*Petiole, color.*—Red, about RHS 46 A.

*Cyathia.*—Few, about 10 in a narrow cluster, about 20–25 mm wide; diameter of the single cythium is 5 mm.

*Color.*—Light to medium-green, RHS 143 A, with darker, medium-green patches, about RHS 137 D; top is red, about RHS 45 B.

*Retention.*—Relatively good, better than with 'Freedom Red' or 'Fisnova'.

*Nectar cups.*—Small to medium-sized, bright yellow, margin usually without anthocyanin coloring.

Reproductive organs:

*Stamens.*—Red filaments, fertile, yellow pollen.

*Pistils.*—Style and stigma are red, 6-lobed stigma.

*Ovaries.*—Triangular, 3 ovules.

Fruit production:

*Seed set/fruit.*—Few seeds are formed spontaneously, but fertile when pollinated; shape and development: typical for the species.

I claim:

1. A new and distinct poinsettia plant named 'Fisgala', substantially as illustrated and described.

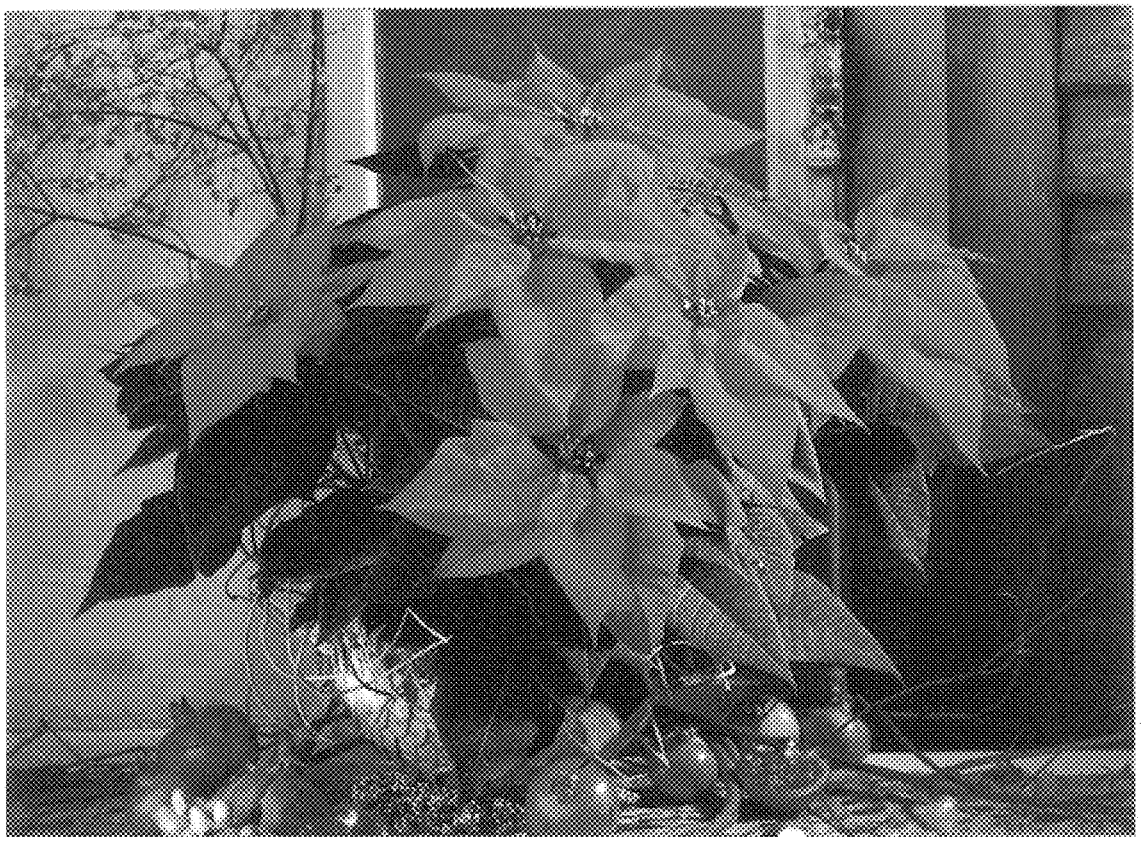

* * * * *